(12) United States Patent
Wei et al.

(10) Patent No.: US 7,867,962 B2
(45) Date of Patent: *Jan. 11, 2011

(54) STRIPED LIQUID PERSONAL CLEANSING ARTICLE CONTAINING A CLEANSING PHASE AND A SEPARATE BENEFIT PHASE COMPRISING A HIGH INTERNAL PHASE EMULSION

(75) Inventors: Karl Shiqing Wei, Mason, OH (US); Cheyne Pohlman Thomas, Independence, KY (US); Mark Richard Sine, New Richmond, OH (US); William Joseph Monsueir, West Chester, OH (US); George Endel Deckner, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/837,201

(22) Filed: Apr. 30, 2004

(65) Prior Publication Data

US 2004/0235693 A1 Nov. 25, 2004

Related U.S. Application Data

(60) Provisional application No. 60/467,207, filed on May 1, 2003.

(51) Int. Cl.
*A61K 7/00* (2006.01)
(52) U.S. Cl. .................. 510/130; 510/136; 510/138; 510/156; 510/424; 510/426; 510/428
(58) Field of Classification Search .............. 510/130, 510/156, 153, 447, 463, 417
See application file for complete search history.

(56) References Cited

U.S. PATENT DOCUMENTS

| | | | |
|---|---|---|---|
| 3,479,429 A | 11/1969 | Morshauser et al. | |
| 3,533,955 A | 10/1970 | Pader et al. | |
| 3,937,811 A | 2/1976 | Papantoniou et al. | |
| 3,980,767 A | 9/1976 | Chown et al. | |
| 4,159,028 A | 6/1979 | Barker et al. | |
| 4,263,363 A | 4/1981 | Buck et al. | |
| 4,335,103 A | 6/1982 | Baker et al. | |
| 4,425,322 A | 1/1984 | Harvey et al. | |
| 4,518,578 A | 5/1985 | Hayes et al. | |
| 4,966,205 A | 10/1990 | Tanaka | |
| 4,980,155 A | 12/1990 | Shah et al. | |
| 5,059,414 A | 10/1991 | Dallal et al. | |
| 5,304,334 A | 4/1994 | Lahanas et al. | |
| 5,393,450 A | 2/1995 | Shana'a et al. | |
| 5,455,035 A | 10/1995 | Guerrero et al. | |
| 5,556,628 A | 9/1996 | Derian et al. | |
| 5,612,307 A | 3/1997 | Chambers et al. | |
| 5,635,171 A | 6/1997 | Nadaud et al. | |
| 5,851,978 A | 12/1998 | Shana'a | |
| 5,929,019 A | 7/1999 | Puvvada et al. | |
| 5,947,335 A | 9/1999 | Milio et al. | |
| 5,952,286 A | 9/1999 | Puvvada et al. | |
| 5,965,500 A | 10/1999 | Puvvada | |
| 5,965,501 A * | 10/1999 | Rattinger et al. | 510/146 |
| 6,174,845 B1 * | 1/2001 | Rattinger et al. | 510/146 |
| 6,176,391 B1 | 1/2001 | Rehkemper et al. | |
| 6,176,395 B1 | 1/2001 | Abbott et al. | |
| 6,213,166 B1 | 4/2001 | Thibiant et al. | |
| 6,245,344 B1 | 6/2001 | Thibiant et al. | |
| 6,268,322 B1 | 7/2001 | St. Lewis et al. | |
| 6,306,806 B1 * | 10/2001 | St. Lewis et al. | 510/159 |
| 6,383,999 B1 | 5/2002 | Coyle et al. | |
| 6,429,177 B1 | 8/2002 | Williams et al. | |
| 6,506,391 B1 | 1/2003 | Biatry | |
| 6,521,216 B1 | 2/2003 | Glandorf et al. | |
| 6,534,456 B2 | 3/2003 | Hayward et al. | |
| 6,534,457 B2 | 3/2003 | Mitra | |
| 6,589,509 B2 | 7/2003 | Keller et al. | |
| 6,673,755 B2 | 1/2004 | Wei et al. | |
| 2001/0036467 A1 | 11/2001 | Thibiant et al. | |
| 2002/0004468 A1 | 1/2002 | Hodge et al. | |
| 2002/0010110 A1 | 1/2002 | Hayward et al. | |
| 2003/0152540 A1 | 8/2003 | Putman et al. | |
| 2003/0180246 A1 | 9/2003 | Frantz et al. | |
| 2004/0048757 A1 | 3/2004 | Zhang et al. | |

(Continued)

FOREIGN PATENT DOCUMENTS

CA 2246316 6/1998

(Continued)

OTHER PUBLICATIONS

XP 002332778 "Dove All Day Moisturizing Body Wash" Online URL: http://www.ewg.org/reprots/skindeep/productinfo.php?prod_id=901910.

(Continued)

*Primary Examiner*—Necholus Ogden, Jr.
(74) *Attorney, Agent, or Firm*—Mark A. Charles; Cynthia L. Clay

(57) ABSTRACT

Personal cleansing compositions that comprise (A) a cleansing phase containing a surfactant and water; and (B) a separate benefit phase comprising at least one high internal phase emulsion; wherein the cleansing and benefit phases are packaged together and are in physical contact. These compositions and corresponding methods provide improved cosmetics, skin feel, and/or skin benefit efficacy.

34 Claims, No Drawings

U.S. PATENT DOCUMENTS

| | | |
|---|---|---|
| 2004/0048758 A1 | 3/2004 | Zhang et al. |
| 2004/0092415 A1* | 5/2004 | Focht et al. ............... 510/130 |
| 2004/0223929 A1 | 11/2004 | Clapp et al. |
| 2004/0242706 A1 | 12/2004 | Wiersema et al. |
| 2004/0248749 A1 | 12/2004 | Mitra et al. |
| 2005/0020468 A1 | 1/2005 | Frantz et al. |
| 2005/0249758 A1 | 11/2005 | Di Puccio Pagano |

FOREIGN PATENT DOCUMENTS

| | | |
|---|---|---|
| DE | 19650952 A | 6/1998 |
| DE | 198 54 086 A | 5/2000 |
| EP | 0 078138 A2 | 5/1983 |
| EP | 0 331617 B | 4/1992 |
| EP | 1 005849 B1 | 9/2001 |
| EP | 0 907345 B1 | 5/2003 |
| GB | 1277324 A | 6/1972 |
| JP | 2000229817 A | 8/2000 |
| JP | 2002-255740 | 9/2002 |
| WO | WO 90/13283 A1 | 11/1990 |
| WO | WO 94/10973 A1 | 5/1994 |
| WO | WO 97/17938 A1 | 5/1997 |
| WO | WO 98/27193 A1 | 6/1998 |
| WO | WO 98/33477 | 8/1998 |
| WO | WO 99/38489 A1 | 8/1999 |
| WO | WO 99/38491 A1 | 8/1999 |
| WO | WO 01/01931 A2 | 1/2001 |
| WO | WO 01/70926 A1 | 9/2001 |
| WO | WO 02/100358 A1 | 12/2002 |
| WO | WO 03/055456 A1 | 7/2003 |
| WO | WO 03/105796 A1 | 12/2003 |
| WO | WO 2004/018609 A1 | 3/2004 |
| WO | WO 2004/026276 A1 | 4/2004 |
| WO | WO 2004/050055 A1 | 6/2004 |
| WO | WO 2005/067875 A1 | 7/2005 |

OTHER PUBLICATIONS

XP002332779 "Olay Daily Renewal Moisturizing Body Wash" Online URL: http://householdprdoucts.nlm.nih.gov/cgi-bin/household.brands?tbl=brands&id=16003084.

* cited by examiner

STRIPED LIQUID PERSONAL CLEANSING ARTICLE CONTAINING A CLEANSING PHASE AND A SEPARATE BENEFIT PHASE COMPRISING A HIGH INTERNAL PHASE EMULSION

CROSS REFERENCE TO RELATED APPLICATION(S)

This application claims the benefit of U.S. Provisional Application No. 60/467,207, filed May 1, 2003.

FIELD OF THE INVENTION

The present invention relates to striped liquid personal cleansing compositions comprising a cleansing phase and a separate benefit phase comprising a high internal phase emulsion wherein the two phases are packaged in physical contact while remaining stable for long periods of time.

BACKGROUND OF THE INVENTION

Personal cleansing compositions that purport to provide skin-conditioning benefits are known. Many of these compositions are aqueous systems comprising an emulsified conditioning oil or other similar materials in combination with a lathering surfactant. Although many of these products provide both conditioning and cleansing benefits, there are often trade-offs associated with their use. For instance, it can be difficult to formulate a stable product that deposits a sufficient amount of skin conditioning agents on skin during use. In order to combat emulsification of the skin conditioning agents by the cleansing surfactant, large amounts of the skin conditioning agent are often added to the compositions. Unfortunately, raising the level of skin conditioning agent in order to achieve increased deposition can negatively affect product lather performance and stability.

One attempt at providing conditioning and cleansing benefits from a personal cleansing product while maintaining stability has been the use of dual-chamber packaging. These packages comprise separate cleansing compositions and conditioning compositions, and allow for the co-dispensing of the two in a single or dual stream. The separate conditioning and cleansing compositions thus remain physically separate and stable during prolonged storage and just prior to application, but then mix during or after dispensing to provide conditioning and cleansing benefits from a physically stable system. Although such dual-chamber delivery systems provide improved conditioning benefits versus conventional systems, it is often difficult to achieve consistent and uniform performance because of the uneven dispensing ratio between the cleansing phase and the conditioning phase from these dual-chamber packages. Additionally, these packaging systems add considerable cost to the finished product.

Striped personal cleaning compositions are also known in the art. However, these compositions do not contain a cleansing phase and a benefit phase and thus stability has not been an issue for these products.

Accordingly, the need still remains for stable personal cleansing compositions that provide both cleansing and improved skin conditioning benefits. It has now been found that striped personal cleansing compositions comprising two phases in physical contact that remain stable for long periods of time can be formulated.

These striped personal cleansing compositions comprise cleansing and benefit phases that are packaged so that the two separate phases are in physical contact yet remain stable. The compositions provide improved deposition of conditioning agents on skin.

The compositions of the present invention further provide improved cosmetics via the striped appearance and improved skin feel during and after application. It has been found that such compositions with separate phase in physical contact can be formulated with sufficiently high levels of benefit agents without compromising product lather performance and stability. The superior lather performance can be demonstrated via the lather volume method described herein.

It has also been found that the striped personal cleansing compositions can be formulated with selected skin active agents that provide improved chronic skin benefits to the skin. These compositions comprise a cleansing phase containing a cleansing surfactant and at least one additional benefit phase containing a high internal phase emulsion and a skin active agent, wherein the cleansing and active phases are packaged in physical contact while remaining stable for long periods of time.

SUMMARY OF THE INVENTION

The present invention is directed to striped personal cleansing compositions comprising a first stripe comprising a cleansing phase comprising a surfactant, and water and at least one additional stripe comprising a separate benefit phase comprising a high internal phase emulsion.

The present invention further relates to a striped personal cleansing composition comprising a cleansing phase and benefit phase wherein at least one phase contains a colorant, wherein both phases are packed in a single package such that the two phases visually form a pattern.

The present invention is also directed to a method of cleansing and moisturizing the skin by applying to the skin a composition as described above.

DETAILED DESCRIPTION

The striped personal cleansing compositions of the present invention comprise, a first stripe comprising a cleansing phase, and at least one additional stripe comprising a benefit phase. The benefit phase comprises a high internal phase emulsion. These and other essential limitations of the compositions and methods of the present invention, as well as many of the optional ingredients suitable for use herein, are described in detail hereinafter.

By the term "stripe" as used herein, is meant that the cleansing phase and the benefit phases herein occupy separate but distinct physical spaces inside the package in which they are stored, but are in direct contact with one another (i.e. they are not separated by a barrier and they are not emulsified or mixed to any significant degree). In one preferred embodiment of the present invention, the cleansing phase and the benefit phase are present within the container as distinct layers or "stripes". The stripes may be relatively uniform and even across the dimension of the package. Alternatively, the layers may be uneven, i.e. wavy, or may be nonuniform in dimension. The stripes do not need to necessarily extend across the entire dimension of the package. The "stripe' can be various geometric shapes, various different colors or include glitter or pearlescence.

The term "high internal phase emulsion" as used herein, unless otherwise specified, refers to those emulsions containing 50% or more of a discontinuous or "internal" phase and 50% or less of a continuous phase. In the compositions herein, the oil phase is the discontinuous phase and the aqueous phase is the continuous phase.

The term "ambient conditions" as used herein, unless otherwise specified, refers to surrounding conditions at one (1) atmosphere of pressure, 50% relative humidity, and 25° C.

The term "stable" as used herein, unless otherwise specified, refers to compositions that maintain at least two "separate" phases when sitting in physical contact at ambient conditions for a period of at least about 180 days. By "separate" is meant that there is substantially no mixing of the phases, observable to the naked eye, prior to dispensing of the composition.

The term "personal cleansing composition" as used herein, unless otherwise specified, refers to compositions intended for topical application to the skin or hair.

The phrase "substantially free of" as used herein, unless otherwise specified means that the compositions comprise less than about 3%, preferably less than about 1%, more preferably less than about 0.5%, even more preferably less than about 0.25%, and most preferably less than about 0.1% of the stated ingredient.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

All cited references are incorporated herein by reference in their entireties. Citation of any reference is not an admission regarding any determination as to its availability as prior art to the claimed invention.

The personal cleansing compositions and methods of the present invention can comprise, consist of, or consist essentially of, the essential elements and limitations of the invention described herein, as well as any additional or optional ingredients, components, or limitations described herein or otherwise useful in personal cleansing compositions intended for topical application to the hair or skin.

Product Form

The personal cleansing compositions of the present invention are typically in the form of a liquid. The term "liquid" as used herein means that the composition is generally flowable to some degree. "Liquids", therefore, can include liquid, semi-liquid, cream, lotion or gel compositions intended for topical application to skin. These compositions typically exhibit a viscosity of equal to or greater than about 3,000 cps to about 1,000,000 cps. These compositions contain a cleansing phase and a benefit phase, both of which are described in greater detail hereinafter.

All of the product forms contemplated for purposes of defining the compositions and methods of the present invention are rinse-off formulations, by which is meant the product is applied topically to the skin or hair and then subsequently (i.e., within minutes) rinsed away with water, or otherwise wiped off using a substrate or other suitable removal means.

Cleansing Phase

The personal cleansing compositions of the present invention comprise an aqueous cleansing phase that contains a surfactant suitable for application to the skin or hair. Suitable surfactants for use herein include any known or otherwise effective cleansing surfactant which are suitable for application to the skin, and which are otherwise compatible with the other essential ingredients in the aqueous cleansing phase of the compositions. These cleansing surfactants include anionic, nonionic, cationic, zwitterionic or amphoteric surfactants, or combinations thereof. Other suitable surfactants are described in McCutcheon's, Emulsifiers and Detergents, 1989 Annual, published by M. C. Publishing Co., and in U.S. Pat. No. 3,929,678.

The aqueous cleansing phase of the personal care compositions preferably comprises a cleansing surfactant at concentrations ranging from about 3% to about 60%, more preferably from about 4% to about 30%, even more preferably from about 5% to about 25%, by weight of the aqueous cleansing phase. The preferred pH range of the cleansing phase is from about 5 to about 8. Frequently surfactants are sold as solutions in water or other solvents which dilute them to less than 100% active surfactant. Therefore the "active surfactant" means actual amount of surfactant delivered to the free flowing composition from a commercial surfactant preparation.

The aqueous cleansing phase of the personal care compositions preferably produces a Total Lather Volume of at least 350 ml, more preferably greater than 400 ml, even more preferably greater than about 600 ml, as described in the Lathering Volume Test. The aqueous cleansing phase of the personal care compositions preferably produces a Flash Lather Volume of at least 150 ml, preferably greater than 200 ml, most preferably greater than 300 ml as described in the Lathering Volume Test.

Anionic surfactants suitable for use in the cleansing phase include alkyl and alkyl ether sulfates. These materials have the respective formula $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine. The alkyl ether sulfates are typically made as condensation products of ethylene oxide and monohydric alcohols having from about 8 to about 24 carbon atoms. Preferably, R has from about 10 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with about 1 to about 10, preferably from about 3 to about 5, and more preferably with about 3, molar proportions of ethylene oxide and the resulting mixture of molecular species having, for example, an average of 3 moles of ethylene oxide per mole of alcohol, is sulfated and neutralized.

Other suitable anionic surfactants include water-soluble salts of the organic, sulfuric acid reaction products of the general formula $[R^1—SO_3-M]$, wherein $R^1$ is chosen from the group consisting of a straight or branched chain, saturated aliphatic hydrocarbon radical having from about 8 to about 24, preferably about 10 to about 18, carbon atoms; and M is a cation. Suitable examples are the salts of an organic sulfuric acid reaction product of a hydrocarbon of the methane series, including iso-, neo-, ineso-, and n-paraffins, having about 8 to about 24 carbon atoms, preferably about 10 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{10-18}$ n-paraffins.

Preferred anionic surfactants for use in the cleansing phase include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and combinations thereof.

Amphoteric surfactants suitable for use in the cleansing phase include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378.

Zwitterionic surfactants suitable for use in the cleansing phase include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Such suitable zwitterionic surfactants can be represented by the formula:

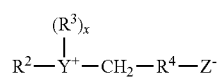

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionic surfactants suitable for use in the cleansing phase include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

Cationic surfactants can also be used in the cleansing phase, but are generally less preferred, and preferably represent less than about 5% by weight of the compositions.

Suitable nonionic surfactants for use in the aqueous cleansing phase include condensation products of alkylene oxide groups (hydrophilic in nature) with an organic hydrophobic compound, which may be aliphatic or alkyl aromatic in nature.

Characteristics of Cleansing Phase Preferred for Stability

Lamellar Structurant

The compositions of the present invention preferably comprise about 0.1% to 10% by wt. of a structurant agent in the cleansing phase which functions in the compositions to form a lamellar phase. It is believed the lamellar phase enhances the interfacial stability between the surfactant phase and the benefit phase.

Suitable structurants includes a fatty acid or ester derivatives thereof, a fatty alcohol, or trihydroxystearin, polycare 133. Most preferably the structurant is selected from lauric acid or trihydroxystearin.

In another preferred embodiment of the present invention the surfactant compositions for use in the cleansing phase exhibit Non-Newtonian shear thinning behavior (herein referred to as free flowing compositions). These surfactant compositions comprise water, at least one anionic surfactant, an electrolyte and at least one alkanolamide. It has been found that by employing a cleansing phase exhibiting Non-Newtonian shear thinning behavior, the stability of the resulting personal cleansing composition may be increased.

The alkanolamide if present has the general structure of:

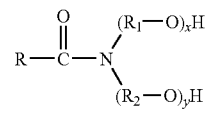

wherein R is $C_8$ to $C_{24}$ or preferably in some embodiments $C_8$ to $C_{22}$ or in other embodiments $C_8$ to $C_{18\ saturated}$ or unsaturated straight chain or branched aliphatic group, $R_1$ and $R_2$ are the same or different $C_2$-$C_4$ straight chain or branched aliphatic group, x=0 to 10; y=1-10 and wherein the sum of x and y is less than or equal to 10.

The amount of alkanolamide in the composition is typically about 0.1% to about 10% by weight, and in some embodiments is preferably about 2% to about 5% by weight of the cleansing phase. Some preferred alkanolamides include Cocamide MEA (Coco monethanolamine) and Cocamide MIPA (Coco monoisopropranolamide).

The electrolyte, if used, can be added per se to the composition or it can be formed in situ via the counter-ions included in one of the raw materials. The electrolyte preferably includes an anion comprising phosphate, chloride, sulfate or citrate and a cation comprising sodium, ammonium, potassium, magnesium or mixtures thereof. Some preferred electrolytes are sodium or ammonium chloride or sodium or ammonium sulfate.

The electrolyte, when present, should be present in an amount, which facilitates formation of the free flowing composition. Generally, this amount is from about 0.1% by weight to about 15% by weight, preferably from about 1% to about 6% by weight of the cleansing phase, but may be varied if required.

Optional Ingredients for Use in the Cleansing Phase

Other suitable, optional ingredients, which may be employed in the cleansing phase, include humectants and solutes. A variety of humectants and solutes can be employed and can be present at a level of from about 0.1% to about 50%, preferably from about 0.5% to about 35%, and more preferably from about 2% to about 20% of a personal care composition.

Nonionic polyethylene/polypropylene glycol polymers are preferably used as skin conditioning agents. Polymers useful herein that are especially preferred are PEG-2M wherein x equals 2 and n has an average value of about 2,000 (PEG 2-M is also known as Polyox WSR® N-10 from Union Carbide and as PEG-2, 000); PEG-SM wherein x equals 2 and n has an average value of about 5,000 (PEG 5-M is also known as Polyox WSR® 35 and Polyox WSR® N-80, both from Union Carbide and as PEG-5, 000 and Polyethylene Glycol 200, 000); PEG-7M wherein x equals 2 and n has an average value of about 7,000 (PEG 7-M is also known as Polyox WSR® (N-750 from Union Carbide); PEG-9M wherein x equals 2 and n has an average value of about 9,000 (PEG 9-M is also known as Polyox WSR® N-3333 from Union Carbide); PEG-14 M wherein x equals 2 and n has an average value of about 14,000 (PEG 14-M is also known as Polyox WSR-205 and Polyox WSR® N-3000 both from Union Carbide); and PEG-90M wherein x equals 2 and n has an average value of about 90,000 (PEG-90M is also known as Polyox WSR®-301 from Union Carbide.)

The striped personal cleansing compositions of the present invention may additionally comprise an organic cationic deposition polymer in the cleansing phase as a deposition aid for the benefit agents described hereinafter. Concentrations of the cationic deposition polymer preferably range from about 0.025% to about 3%, more preferably from about 0.05% to about 2%, even more preferably from about 0.1% to about 1%, by weight of the cleansing phase composition.

Suitable cationic deposition polymers for use in the striped personal cleansing composition of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the personal cleansing composition. The average molecular weight of the cationic deposition polymer is between about 5,000 to about 10 million, preferably at least about 100,000, more preferably at least about 200,000, but preferably not more than about 2 million, more preferably not more than about 1.5 million. The polymers also have a cationic charge density ranging from about 0.2 meq/gm to about 5 meq/gm, preferably at least about 0.4 meq/gm, more preferably at least about 0.6 meq/gm, at the pH of intended use of the personal cleansing composition, which pH will generally range from about pH 4 to about pH 9, preferably between about pH 5 and about pH 8.

Nonlimiting examples of cationic deposition polymers for use in the personal cleansing composition include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquaternium 10 which are available from Amerchol Corp. (Edison, N.J., USA) in their Polymer KG, JR and LR series of polymers with the most preferred being KG-30M.

Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Aqualon.

Other suitable cationic deposition polymers include synthetic cationic polymers. The cationic polymers suitable for use in the cleansing composition herein are water soluble or dispersible, non crosslinked, cationic polymers having a cationic charge density of from about 4 meq/gm to about 7 meq/gm, preferably from about 4 meq/gm to about 6 meq/gm, more preferably from about 4.2 meq/gm to about 5.5 meq/gm. The select polymers also must have an average molecular weight of from about 1,000 to about 1 million, preferably from about 10,000 to about 500,000, more preferably from about 75,000 to about 250,000.

The concentration of the cationic polymer in the cleansing composition ranges about 0.025% to about 5%, preferably from about 0.1% to about 3%, more preferably from about 0.2% to about 1%, by weight of the composition.

A non limiting example of a commercially available synthetic cationic polymer for use in the cleansing compositions is polymethyacrylamidopropyl trimonium chloride, available under the trade name Polycare 133, from Rhodia, Cranberry, N.J., U.S.A.

The cationic polymers herein are either soluble in the cleansing phase, or preferably are soluble in a complex coacervate phase in the striped personal cleansing composition formed by the cationic deposition polymer and the anionic surfactant component described hereinbefore. Complex coacervates of the cationic deposition polymer can also be formed with other charged materials in the personal cleansing composition.

Coacervate formation is dependent upon a variety of criteria such as molecular weight, component concentration, and ratio of interacting ionic components, ionic strength (including, modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", Cosmetics & Toiletries, Vol. 106, April 1991, pp 49-54, C. J. van Oss, "Coacervation, Complex-Coacervation and Flocculation", J. Dispersion Science and Technology, Vol. 9 (5,6), 1988-89, pp 561-573, and D. J. Burgess, "Practical Analysis of Complex Coacervate Systems", J. of Colloid anti Interface Science, Vol. 140, No. 1, November 1990, pp 227-238, which descriptions are incorporated herein by reference.

It is believed to be particularly advantageous for the cationic deposition polymer to be present in the personal cleansing composition in a coacervate phase, or to form a coacervate phase upon application or rinsing of the cleansing composition to or from the skin. Complex coacervates are believed to more readily deposit on the skin, which results in improved deposition of the benefit materials. Thus, in general, it is preferred that the cationic deposition polymer exists in the personal cleansing composition as a coacervate phase or form a coacervate phase upon dilution. If not already a coacervate in the personal cleansing composition, the cationic deposition polymer will preferably exist in a complex coacervate form in the cleansing composition upon dilution with water.

Techniques for analysis of formation of complex coacervates are known in the art. For example, centrifugation analyses of the personal cleansing compositions, at any chosen stage of dilution, can be utilized to identify whether a coacervate phase has formed.

Other non limiting examples of these optional ingredients include vitamins and derivatives thereof (e.g., ascorbic acid, vitamin E, tocopheryl acetate, and the like); sunscreens;

thickening agents (e.g., polyol alkoxy ester, available as Crothix from Croda); preservatives for maintaining the anti microbial integrity of the cleansing compositions; anti-acne medicaments (resorcinol, salicylic acid, and the like); anti-oxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), lakes, colorings, and the like (e.g., clove oil, menthol, camphor, eucalyptus oil, and eugenol).

Benefit Phase (High Internal Phase Emulsion)

The benefit phase of the present invention comprises a high internal phase (HIP) emulsion comprising an oil, and aqueous and preferably a stabilizer. The high internal phase emulsion is an emulsion containing 50% or more of a discontinuous or "internal" phase and 50% or less of a continuous phase. The oil phase is the discontinuous phase and the aqueous phase is the continuous phase.

Oils

The benefit phase of the present invention typically comprises from about 50% to about 99% of oil, more preferably 50 to about 95% oil, even more preferably from 55% to about 90% oil and most preferably from 60% to about 80% oil.

In general, the higher the level of oil employed in the HIP emulsion, the more stable the personal cleansing composition employing the HIP emulsion will be. Oils suitable for use herein include any natural and synthetic materials with an overall solubility parameter less than about 12.5 $(cal/cm^3)^{0.5}$, preferably less than about 11.5 $(cal/cm^3)^{0.5}$. Solubility parameters for the oils described herein are determined by methods well known in the chemical arts for establishing the relative polar character of a material. A description of solubility parameters and means for determining them are described by C. D. Vaughn, "Solubility Effects in Product, Package, Penetration and Preservation" 103 Cosmetics and Toiletries 47-69, October 1988; and C. D. Vaughn, "Using Solubility Parameters in Cosmetics Formulation", 36 J. Soc. Cosmetic Chemists 319-333, September/October, 1988.

The benefit agent for use in the benefit phase of the composition has a Vaughan Solubility Parameter (VSP) of from about 5 to about 10 $(cal/cm^3)^{0.5}$, preferably from about 6 to less than 10 $(cal/cm^3)^{0.5}$, more preferably from about 6 to about 9 $(cal/cm^3)^{0.5}$. Non-limiting examples of benefit agents having VSP values ranging from about 5 to about 10 $(cal/cm^3)^{0.5}$ include the following:

VAUGHAN SOLUBILITY PARAMETERS*$(cal/cm^3)^{0.5}$

| | |
|---|---|
| Cyclomethicone | 5.92 |
| Squalene | 6.03 |
| Petrolatum | 7.33 |
| Isopropyl Palmitate | 7.78 |
| Isopropyl Myristate | 8.02 |
| Castor Oil | 8.90 |
| Cholesterol | 9.55 |

As reported in Solubility, Effects in Product, Package, Penetration and Preservation, C. D. Vaughan, Cosmetics and Toiletries, Vol. 103, October 1988.

By "overall solubility parameter" is meant that it is possible to use oils with higher solubility parameters than 12.5 $(cal/cm^3)^{0.5}$ if they are blended with other oils to reduce the overall solubility parameter of the oil mixture to less than about 12.5 $(cal/cm^3)^{0.5}$. For example, a small portion of diethylene glycol (sol par=13.61) could be blended with lanolin oil (sol par=7.3) and a cosolublizing agent to create a mixture that has a solubility parameter of less than 12.5 $(cal/cm^3)^{0.5}$.

Suitable for use herein oils include but are not limited to, hydrocarbon oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin and its derivatives, wax esters, beeswax derivatives, sterols and phospholipids, and combinations thereof.

Non-limiting examples of hydrocarbon oils and waxes suitable for use herein include petrolatum, mineral oil, microcrystalline waxes, polyalkenes, paraffins, cerasin, ozokerite, polyethylene, perhydrosqualene, poly alpha olefins, hydrogenated polyisobutenes and combinations thereof.

Non-limiting examples of silicone oils suitable for use herein include dimethicone copolyol, dimethylpolysiloxane, diethylpolysiloxane, mixed C1-C30 alkyl polysiloxanes, phenyl dimethicone, dimethiconol, and combinations thereof. Preferred are non-volatile silicones selected from dimethicone, dimethiconol, mixed C1-C30 alkyl polysiloxane, and combinations thereof. Nonlimiting examples of silicone oils useful herein are described in U.S. Pat. No. 5,011,681 (Ciotti et al.).

Non-limiting examples of diglycerides and triglycerides suitable for use herein include castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils, sunflower seed oil, and vegetable oil derivatives; coconut oil and derivatized coconut oil, cottonseed oil and derivatized cottonseed oil, jojoba oil, cocoa butter, and combinations thereof. In addition any of the above oils that have been partially or fully hydrogenated are also suitable.

Non-limiting examples of acetoglyceride esters suitable for use herein include acetylated monoglycerides.

Non-limiting examples of alkyl esters suitable for use herein include isopropyl esters of fatty acids and long chain esters of long chain fatty acids, e.g. SEFA (sucrose esters of fatty acids). Lauryl pyrolidone carboxylic acid, pentaerthritol esters, aromatic mono, di or triesters, cetyl ricinoleate, non-limiting examples of which include isopropyl palmitate, isopropyl myristate, cetyl riconoleate and stearyl riconoleate. Other examples are: hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of alkenyl esters suitable for use herein include oleyl myristate, oleyl stearate, oleyl oleate, and combinations thereof.

Non-limiting examples of lanolin and lanolin derivatives suitable for use herein include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, hydroxylated lanolin, hydrogenated lanolin and combinations thereof.

Still other suitable oils include milk triglycerides (e.g., hydroxylated milk glyceride) and polyol fatty acid polyesters.

Still other suitable oils include wax esters, non-limiting examples of which include beeswax and beeswax derivatives, spermaceti, myristyl myristate, stearyl stearate, and combinations thereof. Also useful are vegetable waxes such as carnauba and candelilla waxes; sterols such as cholesterol, cholesterol fatty acid esters; and phospholipids such as lecithin and derivatives, sphingo lipids, ceramides, glycosphingo lipids, and combinations thereof.

Stabilizers

The benefit phase of the present invention typically comprises from about 0.1% to about 10% of a stabilizer, preferably from about 0.5% to about 5%, and more preferably from about 0.5% to about 3%. Preferred stabilizers are those that reduce the surface tension of water to not less 60 mN/m at 25° C. as measured by standard surface tension apparati and methods known to those of ordinary skill in the art, for example ASTM D1331-89 (2001) Method A, "Surface Tension". Preferred stabilizers exhibit a minimum surface tension in water of 60 mN/m or higher. Suitable stabilizers promote stability of the oil in water emulsion by inhibiting coalescence of the oil droplets, and/or inhibiting phase separation of the oil and water phases.

Some suitable stabilizers are Pemulen TR-1 (Acrylates/C10-30 Alkyl Acrylate Crosspolymer-Noveon), Pemulen TR-2 (Acrylates/C10-30 Alkyl Acrylate Crosspolymer-Noveon), ETD 2020 (Acrylates/C10-30 Alkyl Acrylate Crosspolymer-Noveon), Carbopol 1382 (Acrylates/C10-30 Alkyl Acrylate Crosspolymer-Noveon), Natrosol CS Plus 330, 430, Polysurf 67 (Cetyl Hydroxyethyl Cellulose-Hercules), Aculyn 22 (Acrylates/Steareth-20 Methacrylate Copolymer-Rohm&Haas) Aculyn 25 (Acrylates/Laureth-25 Methacrylate copolymer-Rohm&Haas), Aculyn 28 (Acrylates/Beheneth-25 Methacrylate copolymer-Rohm&Haas), Aculyn 46 (Peg-150/Stearyl Alcohol/SMDI copolymer-Rohm&Haas) Stabylen 30 (Acrylates/Vinyl Isodecanoate-3V), Structure 2001 (Acrylates/Steareth-20 Itaconate copolymer-National Starch), Structure 3001 (Acrylates/Ceteth-20 Itaconate copolymer-National Starch), Structure Plus (Acrylates/Aminoacrylates/C10-30 Alkyl Peg 20 Itaconate copolymer-National Starch, Quatrisoft LM-200 (Polyquaternium-24), the metal oxides of titanium, zinc, iron, zirconium, silicon, manganese, aluminium and cerium, polycarbonates, polyethers, polyethylenes, polypropylenes, polyvinyl chloride, polystyrene, polyamides, polyacrylates, cyclodextrins and mixtures thereof.

Cyclodextrins are solubilized, water-soluble, uncomplexed cyclodextrins. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. Examples of preferred water-soluble cyclodextrin derivatives suitable for use herein are hydroxypropyl alpha-cyclodextrin, methylated alpha-cyclodextrin, methylated beta-cyclodextrin, hydroxyethyl beta-cyclodextrin, and hydroxypropyl beta-cyclodextrin.

It is also preferable to use a mixture of cyclodextrins. Such mixtures can complex with a wider range of perfume molecules having a wider range of molecular sizes. Preferably at least a portion of the cyclodextrins is alpha-cyclodextrin and its derivatives thereof, gamma-cyclodextrin and its derivatives thereof, and/or derivatised beta-cyclodextrin, and mixtures thereof.

Cyclodextrins particularly preferred for use herein are alpha cyclodextron, beta cyclodextron, hydroxypropyl alpha cyclodextrin, hydroxypropyl beta cyclodextrin, and a mixture thereof.

Suitable stabilizers also include nonionic surfactants, cationic surfactants, and anionic surfactants. Examples of suitable surfactants include polyglycerol-10 laurate (Dacaglyn 10L from Nikko Chemical), decyl glucoside (Plantaren 2000 from Cognis), octyl dodeceth 20 (Hetexol 120-20 from Global Seven), Laureth 7 (from Global Seven), sodium trideceth 3 carboxylate (ECTD-3NEX from Nikko Chemical).

Other suitable stabilizers include sub-micron organic or inorganic particles absorbed at the interface. Examples of suitable particles include micronized zeolite, fumed silica, titanium dioxide, zinc oxide, and aluminium oxide.

Aqueous Phase

The benefit phase of the present invention typically comprises from about 1% to about 50% of aqueous phase. The term aqueous comprises a fluid selected from the group consisting of water, mono- and polyhydric alcohols (glycerin, propylene glycol, ethanol, isopropanol, etc.).

Method of Use

The striped personal cleansing compositions of the present invention are preferably applied topically to the desired area of the skin or hair in an amount sufficient to provide effective delivery of the skin conditioning agent to the applied surface, or to otherwise provide effective skin conditioning benefits. The compositions can be applied directly to the skin or indirectly via the use of a cleansing puff, washcloth, sponge or other implement. The compositions are preferably diluted with water prior to, during, or after topical application, and then subsequently rinsed or wiped off of the applied surface, preferably rinsed off of the applied surface using water or a water-insoluble substrate in combination with water.

Method of Manufacture

The personal cleansing compositions of the present invention may be prepared by any known or otherwise effective technique, suitable for making and formulating the desired striped product form. It is effective to combine toothpaste-tube filling technology with a spinning stage design. Additionally, the present invention can be prepared by the method and apparatus as disclosed in U.S. Pat. No. 6,213,166, herein incorporated by reference. The method and apparatus allows two or more compositions to be filled with a spiral configuration into a single container. The method requires that at least two nozzles be employed to fill the container. The container is placed on a static mixer and spun as the composition is introduced into the container.

Alternatively, it is especially effective to combine at least two phases by first placing the separate compositions in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The next step involves pumping the product that was mixed in the blending section via a hose into a single nozzle, then placing the nozzle into a container and filing the container with the resulting product. Specific non-limiting examples of such methods as they are applied to specific embodiments of the present invention are described in the following examples.

If the personal cleansing compositions contain stripes of varying colors it may be desirable to package these compositions in a transparent package such that the consumer can view the pattern through the package. Because of the viscosity of the subject compositions it may also be desirable to include instructions to the consumer to store the package upside down, on its cap to facilitate dispensing.

Analytical Methods

Lather Volume

Lather volume of a striped liquid personal cleansing composition is measured using a graduated cylinder and a tumbling apparatus. A 1,000 ml graduated cylinder is chosen which is marked in 10 ml increments and has a height of 14.5 inches at the 1,000 ml mark from the inside of its base (for example, Pyrex No. 2982). Distilled water (100 grams at 23° C.) is added to the graduated cylinder. The cylinder is clamped in a rotating device, which clamps the cylinder with an axis of rotation that transects the center of the graduated cylinder. One gram of the total personal cleansing composition (0.5 g of the cleansing phase and 0.5 g of the benefit phase when measuring the product, or 1.0 g of the cleansing phase when measuring cleansing phase only) is added into the graduated cylinder and the cylinder is capped. The cylinder is rotated at a rate of 10 revolutions in about 20 seconds, and stopped in a vertical position to complete the first rotation sequence. A timer is set to allow 30 seconds for the lather thus generated to drain. After 30 seconds of such drainage, the first lather volume is measured to the nearest 10 ml mark by recording the lather height in ml up from the base (including any water that has drained to the bottom on top of which the lather is floating).

If the top surface of the lather is uneven, the lowest height at which it is possible to see halfway across the graduated cylinder is the first lather volume (ml). If the lather is so coarse that a single or only a few foam cells ("bubbles") reach across the entire cylinder, the height at which at least 10 foam cells are required to fill the space is the first lather volume, also in ml up from the base. Foam cells larger than one inch in any dimension, no matter where they occur, are designated as unfilled air instead of lather. Foam that collects on the top of the graduated cylinder but does not drain is also incorporated in the measurement if the foam on the top is in its own continuous layer, by adding the ml of foam collected there using a ruler to measure thickness of the layer, to the ml of foam measured up from the base. The maximum foam height is 1,000 ml (even if the total foam height exceeds the 1,000 ml mark on the graduated cylinder). One minute after the first rotation is completed, a second rotation sequence is commenced which is identical in speed and duration to the first rotation sequence. The second lather volume is recorded in the same manner as the first, after the same 30 seconds of drainage time. A third sequence is completed and the third lather volume is measured in the same manner, with the same pause between each for drainage and taking the measurement.

The lather result after each sequence is added together and the Total Lather Volume determined as the sum of the three measurements, in ml. The Flash Lather Volume is the result after the first rotation sequence only, in ml, i.e., the first lather volume. Compositions according to the present invention perform significantly better in this test than similar compositions in conventional emulsion form.

Viscosity of the Liquid Personal Cleansing Composition

The Wells-Brookfield Cone/Plate Model DV-II+ Viscometer can be used to determine the viscosity of the liquid personal cleansing compositions herein. The determination is performed at 25 C with the 2.4 cm$^0$ cone measuring system with a gap of 0.013 mm between the two small pins on the respective cone and plate. The measurement is performed by injecting 0.5 ml of the sample, to be analyzed, between the cone and plate and, then, rotating the cone at a set speed of 1 rpm. The resistance to the rotation of the cone produces a torque that is proportional to the shear stress of the liquid sample. The amount of torque is read 2 minutes after loading the sample and computed by the viscometer into absolute centipoise units (mPa*s) based on the geometric constant of the cone, the rate of rotation, and the stress related torque.

Yield Point of Liquid Personal Cleansing Composition

The Carrimed CSL 100 Controlled Stress Rheometer can be used to determine the yield point of the liquid personal cleansing compositions. For purpose herein, the yield point is the amount of stress required to produce a strain of 1% on the liquid personal cleansing composition. The determination is performed at 77 F with the 4 cm 2$^0$ cone measuring system set with a 51 micron gap. The determination is performed via the programmed application of a shear stress (typically from about 0.06 dynes/sq. centimeter to about 500 dynes/sq. centimeter) over time interval of 5 minutes. It is this amount of stress that results in a deformation of the sample, a shear stress vs. strain curve can be created. From this curve, the yield point of the liquid personal cleansing composition can be calculated.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Each of the exemplified compositions provides improved deposition or effectiveness of the skin conditioning agents or optional ingredients delivered from each prepared composition.

Examples 1-3

The following examples described in Table 1 are non-limiting examples of the personal cleansing compositions herein.

TABLE 1

Cleansing Phase and Benefit phase Compositions

| Ingredient | Example 1 wt % | Example 2 wt % | Example 3 Wt % |
| --- | --- | --- | --- |
| I. Cleansing Phase Composition | | | |
| Ammonium Laureth-3 Sulfate | 3.0 | 3.0 | 3.0 |
| Sodium Lauroamphoacetate (Miranol L-32 Ultra from Rhodia) | 16.7 | 16.7 | 16.7 |
| Ammonium Lauryl Sulfate | 1.0 | 1.0 | 1.0 |
| Lauric Acid | 0.9 | 0.9 | 0.9 |
| Trihydroxystearin (Thixcin R) | 2.0 | 2.0 | 2.0 |

TABLE 1-continued

Cleansing Phase and Benefit phase Compositions

| Ingredient | Example 1 wt % | Example 2 wt % | Example 3 Wt % |
|---|---|---|---|
| Guar Hydroxypropyltrimonium Chloride (N-Hance 3196 from Aqualon) | 0.17 | 0.75 | 0.75 |
| Guar Hydroxypropyltrimonium Chloride (Jaguar C-17 from Rhodia) | 0.58 | — | — |
| Polyquaterium 10 (UCARE polymer JR-30 M from Amerchol) | 0.45 | — | — |
| Polymethacrylamidopropyltrimonium Chloride (Polycare 133 from Rhodia) | — | 0.24 | — |
| Polyquaternium-39 (Merqurt Plus 3300 from Calgon) | — | 0.81 | — |
| PEG 90 M (Polyox WSR 301 from Union Carbide) | 0.25 | — | — |
| PEG-14 M (Polyox WSR N-3000 H from Union Carbide) | 0.45 | 2.45 | 2.45 |
| Linoleamidoprypyl PG-Dimonium Chloride Phosphate Dimethicone (Monasil PLN from Uniqema) | — | 1.0 | 4.0 |
| Glycerin | 1.4 | 4.9 | 4.9 |
| Sodium Chloride | 0.3 | 0.3 | 0.3 |
| Sodium Benzoate | 0.25 | 0.25 | 0.25 |
| Disodium EDTA | 0.13 | 0.13 | 0.13 |
| Glydant | 0.37 | 0.37 | 0.37 |
| Citric Acid | 1.6 | 0.95 | 0.95 |
| Titanium Dioxide | 0.5 | 0.5 | 0.5 |
| Perfume | 0.5 | 0.5 | 0.5 |
| Water and Colorant | Q.S. | Q.S. | Q.S. |
| II. Benefit phase Composition | | | |
| Petrolatum (Superwhite Protopet) | 68 | 68 | 68 |
| Cetyl Hydroxyethylcellulos (Natrosol Plus) | 0.91 | 0.91 | 0.91 |
| Water and Minors | Q.S. | Q.S. | Q.S. |

The cleansing phase and benefit phase compositions described above can be prepared by conventional formulation and mixing techniques. The cleansing composition 1 can be prepared by first creating the following premixes: citric acid in water premix at 1:3 ratio, Guar polymer premix with Jaguar C-17 and N-Hance 3196 in water at 1:10 ratio, UCARE premix with JR-30M in water at about 1:30 ratio, and Polyox premix with PEG-90M and PEG-14M in Glycerin at about 1:2 ratio. Then, the following ingredients will be added into the main mixing vessel: ammonium lauryl sulfate, ammonium laureth-3 sulfate, citric acid premix, Miranol L-32 ultra, sodium chloride, sodium benzoate, disodium EDTA, lauric acid, Thixcin R, Guar premix, UCARE premix, Polyox Premix, and the rest of water. Then one will heat the vessel with agitation until it reaches 190° F. (88° C.). Let it mix for about 10 min. Cool the batch with a cold water bath with slow agitation until it reaches 110° F. (43° C.). Add the following ingredients: Glydant, perfume, Titanium Dioxide. Mix until a homogeneous solution forms.

The cleansing composition 2 can be prepared by first creating the following premixes: citric acid in water premix at 1:3 ratio, Guar polymer premix with N-Hance 3196 in water at 1:10 ratio, and Polyox premix with PEG-14M in Glycerin at about 1:2 ratio. Then, the following ingredients will be added into the main mixing vessel: ammonium lauryl sulfate, ammonium laureth-3 sulfate, citric acid premix, Miranol L-32 ultra, sodium chloride, sodium benzoate, disodium EDTA, lauric acid, Thixcin R, Guar premix, Polyox Premix, Polycare 133, Merquat Plus 3300, Monosil PLN, and the rest of water. Then, the vessel will be heated with agitation until it reaches 190° F. (88° C.). Let it mix for about 10 min. Next, the batch will be cooled with a cold water bath with slow agitation until it reaches 110° F. (43° C.). Finally, the following ingredients will be added: Glydant, perfume, Titanium Dioxide and mixed until a homogeneous solution forms.

The cleansing composition 3 can be prepared by first creating the following premixes: citric acid in water premix at 1:3 ratio, Guar polymer premix with N-Hance 3196 in water at 1:10 ratio, and Polyox premix with PEG-14M in Glycerin at about 1:2 ratio. Then, the following ingredients will be added into the main mixing vessel: ammonium lauryl sulfate, ammonium laureth-3 sulfate, citric acid premix, Miranol L-32 ultra, sodium chloride, sodium benzoate, disodium EDTA, lauric acid, Thixcin R, Guar premix, Polyox Premix, Monasil PLN, and the rest of water. Then the vessel will be heated with agitation until it reaches 190° F. (88° C.). The vessel will be mixed for about 10 min. Next, the batch will be cooled with a cold water bath with slow agitation until it reaches 110° F. (43° C.). Finally, the following ingredients will be added: Glydant, perfume, Titanium Dioxide and mixed until a homogeneous solution forms.

Benefit Phase

The benefit phase can be prepared by adding water into the main mixing vessel. Then, the vessel will be heated to 185 F. Then, Natrosol Plus will be slowly added with agitation. The benefit phase will be kept agitating for one hour. In a separate vessel, the petrolatum will be heated to 185 F. The main mixing vessel will have petrolatum slowly added with good agitation. Then, the product will be thoroughly mixed through a high shear mixer until homogeneous.

The cleansing and benefit phases can be packaged into a single container by first placing the separate compositions in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The next step involves pumping the product that was mixed in the blending section via a hose into a single nozzle, then placing the nozzle into a container and filing the container with the resulting product.

Examples 4-6

Examples 4-6 are described in Table 2. Examples 4-6 are non-limiting examples of the personal cleansing compositions herein.

TABLE 2

Cleansing Phase and Benefit phase Compositions

| Ingredient | Example 4 wt % | Example 5 wt % | Example 6 wt % |
|---|---|---|---|
| I. Cleansing Phase Composition | | | |
| Miracare SLB-365 (from Rhodia) (Sodium Trideceth Sulfate, Sodium Lauramphoacetate, Cocamide MEA) | 47.4 | 47.4 | 47.4 |
| Guar Hydroxypropyltrimonium Chloride (N-Hance 3196 from Aqualon) | — | — | 0.7 |
| PEG 90 M (Polyox WSR 301 from Dow Chemical) | — | — | 0.2 |
| Cocamide MEA | 3.0 | — | — |
| Polycare 133 | — | — | 0.4 |
| Lauric Acid | — | 2.0 | 2.0 |
| Sodium Chloride | 3.5 | 3.5 | 3.5 |
| Disodium EDTA | 0.05 | 0.05 | 0.05 |
| Glydant | 0.67 | 0.67 | 0.67 |
| Citric Acid | 0.4 | 0.4 | 0.4 |
| Perfume | 2.0 | 2.0 | 2.0 |
| Water and Colorant (pH) | Q.S. (6.0) | Q.S. (6.0) | Q.S. (6.0) |
| II. Benefit phase Composition | | | |
| Petrolatum (Superwhite Protopet) | 68 | 68 | 68 |
| Cetyl Hydroxyethylcellulos (Natrosol Plus) | 0.91 | 0.91 | 0.91 |
| Water and Minors | Q.S. | Q.S. | Q.S. |

The compositions described above can be prepared by conventional formulation and mixing techniques. The cleansing phase composition can be prepared by first adding citric acid into water at 1:3 ratios to form a citric acid premix. The following ingredients will then be added into the main mixing vessel in the following sequence: water, Miracare SLB-354, sodium chloride, sodium benzoate, Disodium EDTA, glydant. The main mixing vessel will start to be agitated. In a separate mixing vessel, disperse polymers (N-Hance 3196) in water at 1:10 ratio will form a polymer premix. The completely dispersed polymer premix will be added into the main mixing vessel with continuous agitation. Polyox WSR 301 will be dispersed in water and then added to the main mixing vessel. Then, the rest of the water and perfume will be added into the batch. The batch will be kept agitating until a homogenous solution forms.

Benefit Phase

The benefit phase can be prepared by adding water into the main mixing vessel. Then, the vessel will be heated to 185 F. Then, Natrosol Plus will be slowly added with agitation. The benefit phase will be kept agitating for one hour. In a separate vessel, the petrolatum will be heated to 185 F. The main mixing vessel will have petrolatum slowly added with good agitation. Then, the product will be thoroughly mixed through a high shear mixer until homogeneous.

The cleansing and benefit phases are packaged into a single container by first placing the separate compositions in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The next step involves pumping the product that was mixed in the blending section via a hose into a single nozzle, then placing the nozzle into a container and filing the container with the resulting product.

Examples 7-9

Examples 7-9 are described in Table 3. Examples 7-9 are non-limiting examples of the personal cleansing compositions herein.

TABLE 3

Cleansing Phase and Benefit phase Compositions

| Ingredient | Example 7 wt % | Example 8 wt % | Example 9 wt % |
|---|---|---|---|
| I. Cleansing Phase Composition | | | |
| Miracare SLB-365 (from Rhodia) (Sodium Trideceth Sulfate, Sodium Lauramphoacetate, Cocamide MEA) | 47.4 | 47.4 | 47.4 |
| Sodium Chloride | 3.5 | 3.5 | 3.5 |
| Disodium EDTA | 0.05 | 0.05 | 0.05 |
| Glydant | 0.67 | 0.67 | 0.67 |
| Citric Acid | 0.4 | 0.4 | 0.4 |
| Perfume | 2.0 | 2.0 | 2.0 |
| Water and Colorant (pH) | Q.S. (6.0) | Q.S. (6.0) | Q.S. (6.0) |
| II. Benefit phase Composition | | | |
| Isopropyl isostearate | 90 | — | — |
| Plantaren 2000 | 5 | — | — |
| Glycerin | 5 | 4.5 | — |
| Petrolaum | — | 72.8 | 90 |
| Water | — | 18.2 | 7.5 |
| ECTD 3NEX | — | 4.5 | — |
| Miracare SLB-365 (from Rhodia) (Sodium Trideceth Sulfate, Sodium Lauramphoacetate, Cocamide MEA) | — | — | 2.5 |

The compositions described above can be prepared by conventional formulation and mixing techniques. The cleansing phase composition can be prepared by first adding citric acid into water at 1:3 ratio to form a citric acid premix. The following ingredients will be added into the main mixing vessel in the following sequence: water, Miracare SLB-354, sodium chloride, sodium benzoate, Disodium EDTA, glydant. The main mixing vessel will start to be agitated. Then, perfume will be added into the batch. The batch will be kept agitating until a homogenous solution forms.

Benefit Phase

The benefit phase can be prepared by mixing the surfactant/stabilizer (plantareen 2000, ECTD 3NEX, and Miracare SLB-365) in the continuous phase (glycerin and/or water). The batch will then be heated to 185 F, then slowly adds Oil Phase (isopropyl isostearate and petrolatum). The mixture will be high sheared until homogenous.

The cleansing and benefit phases are packaged into a single container by first placing the separate compositions in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The next step involves pumping the product that was mixed in the blending section via a hose into a single nozzle, then placing the nozzle into a container and filing the container with the resulting product.

What is claimed is:

1. A personal cleansing article comprising a package containing a liquid striped personal cleansing composition comprising:
   (a) a first stripe comprising a cleansing phase comprising a surfactant and water; and
   (b) at least one additional stripe comprising a benefit phase comprising a high internal phase emulsion; wherein said high internal phase emulsion comprises:
      (i) 50% or more of an oil; and
      (ii) from about 0.5% to about 3% of a stabilizer,
   wherein the cleansing phase and the benefit phase in physical contact within said package.

2. The personal cleansing article according to claim 1, wherein the cleansing phase comprises:
   (i) at least one anionic surfactant;
   (ii) at least one electrolyte; and
   (iii) at least one alkanolamide;
   wherein the cleansing phase is non-Newtonian shear thinning; and
   the cleansing phase has a viscosity of equal to or greater than about 3000 centipoise.

3. A personal cleansing article according to claim 2, wherein said cleansing phase comprises from about 3% to about 60%, by weight of the cleansing phase, of surfactant.

4. A personal cleansing article according to claim 2, wherein the electrolyte comprises
   i) an anion selected from the group consisting of phosphate, chloride, sulfate, citrate, and mixtures thereof, and
   ii) a cation selected from the group consisting of sodium, ammonium, potassium, magnesium, and mixtures thereof; and wherein the electrolyte is present at a level of from about 0.1% to about 15% by weight of the cleansing phase.

5. A personal cleansing article according to claim 1, wherein said cleansing phase further comprises a cationic deposition polymer.

6. A personal cleansing article according to claim 5, wherein said cationic deposition polymer is selected from the group consisting of cationic cellulosic derivatives, cationic guar derivatives, cationic synthetic polymers, and mixtures thereof.

7. A personal cleansing article according to claim 1, wherein the cleansing phase additionally comprises a lamellar structurant.

8. A personal cleansing article according to claim 7, wherein the lamellar structurant is selected from the group consisting of fatty acids, fatty esters, trihydroxystearin, fatty alcohols, and mixtures thereof.

9. A personal cleansing article according to claim 1, wherein the benefit phase comprises an emulsifier selected from the group consisting of nonionic surfactant, cationic surfactant, anionic surfactant, and mixtures thereof.

10. A personal cleansing article according to claim 1, wherein the oil is selected from the group consisting of hydrocarbon oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin, lanolin derivatives, wax esters, beeswax derivatives, sterols, phospholipids, and mixtures thereof.

11. A personal cleansing article according to claim 1, wherein the stabilizer is selected from the group consisting of acrylates/C10-30 alkyl acrylate crosspolymer, cetyl hydroxyethyl cellulose, acrylate/steareth-20 methacrylate copolymer, acrylate/laureth-25 methacrylate copolymer, acrylate/steareth-20 methacrylate copolymer, acrylate/laureth-25 methacrylate copolymer, acrylate/beheneth-25 methacrylate copolymer, PEG-150/stearyl alcohol/SMDI copolymer, acrylate/vinyl isodecanoate, acrylate/steareth-20 itaconate copolymer, acrylate/ceteth-20 itaconate copolymer, acrylate/aminoacrylate/C10-C30 alkyl PEG-20 itaconate copolymer, polyquaternium-24, the metal oxides of titanium, zinc, iron, zirconium, silicon, manganese, aluminium and cerium, polycarbonates, polyethers, polyethylenes, polypropylenes, polyvinyl chloride, polystyrene, polyamides, polyacrylates, and mixtures thereof.

12. A personal cleansing article according to claim 1, wherein at least one phase contains a colorant.

13. A personal cleansing article according to claim 12, wherein the cleansing and benefit phases visually form a pattern within the package.

14. A personal cleansing article according to claim 13, wherein the pattern is selected from the group consisting of striped, marbled, geometric, and mixtures thereof.

15. A personal cleansing article according to claim 14, wherein said package is transparent.

16. A personal cleansing article according to claim 1, wherein said package comprises a lid; and said package includes instructions to store said package on the lid.

17. A personal cleansing article according to claim 1, wherein the composition additionally comprises skin care actives, wherein the skin care actives are selected from the group consisting of vitamins; vitamin derivatives; sunscreens; preservatives; anti-acne medicaments; antioxidants; skin soothing and healing agents; chelators; and sequestrants; essential oils; skin sensates; and mixtures thereof.

18. A personal cleansing article comprising a package containing a liquid striped personal cleansing composition comprising:
   a) a first stripe comprising a cleansing phase comprising from about 1% to about 50%, by weight of the cleansing phase, of a surfactant selected from the group consisting of anionic surfactant, non-ionic surfactant, zwitterionic surfactant, cationic surfactant, soap and mixtures thereof;
   wherein the cleansing phase is non-Newtonian shear thinning, has a viscosity of equal to or greater than about 3,000 centipoise and a yield point of at least about 0.1 Pascal; and
   b) at least one additional stripe comprising a separate benefit phase comprising a high internal phase emulsion comprising:
      i. 50% or more of an oil,
      ii. from about 0.5% to about 3.0% of a stabilizer,
      iii. and water;
   wherein the ratio of the cleansing phase to the benefit phase is from about 1:9 to about 99:1;
   wherein the cleansing phase and benefit phase are present as stripes wherein the stripe size is at least about 0.1 mm in width and at least about 1 mm in length and wherein the cleansing phase and the benefit phase are in physical contact within said package.

19. A personal cleansing article according to claim 18, wherein the cleansing phase comprises:
   (i) at least one anionic surfactant;
   (ii) at least one electrolyte;

(iii) at least one alkanolamide; and
(iv) water;
wherein the cleansing phase is non-Newtonian shear thinning; and
the cleansing phase has a viscosity of equal to or greater than about 3000 centipoise.

20. A personal cleansing article according to claim 19, wherein said cleansing phase comprises from about 3% to about 60%, by weight of the cleansing phase, of surfactant.

21. A personal cleansing article according to claim 19, wherein the electrolyte comprises
   i) an anion selected from the group consisting of phosphate, chloride, sulfate, citrate, and mixtures thereof, and
   ii) a cation selected from the group consisting of sodium, ammonium, potassium, magnesium, and mixtures thereof; and wherein the electrolyte is present at a level of from about 0.1% to about 15% by weight of the cleansing phase.

22. A personal cleansing article according to claim 18, which additionally comprises a cationic deposition polymer in said cleansing phase.

23. A personal cleansing article according to claim 22, wherein said cationic deposition polymer is selected from the group consisting of cationic cellulosic derivatives, cationic guar derivatives, cationic synthetic polymers, and mixtures thereof.

24. A personal cleansing article according to claim 18, wherein the cleansing phase additionally comprises a lamellar structurant.

25. A personal cleansing article according to claim 18, wherein the lamellar structurant is selected from the group consisting of fatty acids, fatty esters, trihydroxystearin, fatty alcohols, and mixtures thereof.

26. A personal cleansing article according to claim 18, wherein the benefit phase comprises an emulsifier selected from the group consisting of nonionic surfactant, cationic surfactant, anionic surfactant, and mixtures thereof.

27. A personal cleansing article according to claim 18, wherein the oil is selected from the group consisting of hydrocarbon oils, waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin, lanolin derivatives, wax esters, beeswax derivatives, sterols and phospholipids, and mixtures thereof.

28. A personal cleansing article according to claim 18, wherein the stabilizer is selected from the group consisting of acrylates/C10-30 alkyl acrylate crosspolymer, cetyl hydroxyethyl cellulose, acrylate/steareth-20 methacrylate copolymer, acrylate/laureth-25 methacrylate copolymer, acrylate/steareth-20 methacrylate copolymer, acrylate/laureth-25 methacrylate copolymer, acrylate/beheneth-25 methacrylate copolymer, PEG-150/stearyl alcohol/SMDI copolymer, acrylate/vinyl isodecanoate, acrylate/steareth-20 itaconate copolymer, acrylate/ceteth-20 itaconate copolymer, acrylate/aminoacrylate/C10-C30 alkyl PEG-20 itaconate copolymer, polyquaternium-24, the metal oxides of titanium, zinc, iron, zirconium, silicon, manganese, aluminium and cerium, polycarbonates, polyethers, polyethylenes, polypropylenes, polyvinyl chloride, polystyrene, polyamides, polyacrylates, and mixtures thereof.

29. A personal cleansing article according to claim 18, wherein at least one phase contains a colorant.

30. A personal cleansing article according to claim 29, wherein the cleansing and benefit phases visually form a pattern within the package.

31. A personal cleansing article according to claim 30, wherein the pattern is selected from the group consisting of striped, marbled, geometric, and mixtures thereof.

32. A personal cleansing article according to claim 31, wherein said package is transparent.

33. A personal cleansing article according to claim 18, wherein said package comprises a lid; and said package includes instructions to store said package on said lid.

34. A personal cleansing article according to claim 18, wherein the composition additionally comprises skin care actives, wherein the skin care actives are selected from the group consisting of vitamins; vitamin derivatives; sunscreens; preservatives; anti-acne medicaments; antioxidants; skin soothing and healing agents; chelators; and sequestrants; essential oils; skin sensates and mixtures thereof.

* * * * *